(12) United States Patent
Karanam et al.

(10) Patent No.: US 11,430,564 B2
(45) Date of Patent: Aug. 30, 2022

(54) PERSONALIZED PATIENT POSITIONING, VERIFICATION AND TREATMENT (71) Applicant: SHANGHAI UNITED IMAGING INTELLIGENCE CO., LTD., Shanghai (CN)

(72) Inventors: Srikrishna Karanam, Brighton, MA (US); Ziyan Wu, Lexington, MA (US)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 210 days.

(21) Appl. No.: 16/814,373

(22) Filed: Mar. 10, 2020

(65) Prior Publication Data
US 2021/0158932 A1 May 27, 2021

Related U.S. Application Data (60) Provisional application No. 62/941,203, filed on Nov. 27, 2019.

(51) Int. Cl.
G16H 30/40 (2018.01)
G06T 7/00 (2017.01)
(Continued)

(52) U.S. Cl.
CPC ........... *G16H 30/40* (2018.01); *A61B 5/0035* (2013.01); *A61B 5/70* (2013.01); *G06K 9/6217* (2013.01);
(Continued)

(58) Field of Classification Search
CPC ........ G16H 30/40; G16H 10/60; G16H 30/20; G16H 50/20; G16H 50/50; A61B 5/0035;
(Continued)

(56) References Cited

U.S. PATENT DOCUMENTS

2005/0049652 A1* 3/2005 Tong .................. A61N 1/36003
607/48
2009/0136094 A1* 5/2009 Driver .................... G16H 10/60
382/115
(Continued)

FOREIGN PATENT DOCUMENTS

KR 101912343 * 4/2018 ........... A61B 5/1123
KR 20180041881 * 4/2018 ........... A61B 5/1123

OTHER PUBLICATIONS

Wei et al., "Convolutional Pose Machines" CVF, 2016, pp. 4724-1732.
(Continued)

Primary Examiner — Amara Abdi
(74) Attorney, Agent, or Firm — Zhong Law, LLC (57) ABSTRACT A patient's healthcare experience may be enhanced utilizing a system that automatically recognizes the patient based on one or more images of the patient and generates personalized medical assistance information for the patient based on electronic medical records stored for the patient. Such electronic medical records may comprise imagery data and/or non-imagery associated with a medical procedure performed or to be performed for the patient. As such, the imagery and/or non-imagery data may be incorporated into the personalized medical assistance information to provide positioning and/or other types of diagnostic or treatment guidance to the patient or a service provider.

18 Claims, 4 Drawing Sheets (51) Int. Cl.

| | |
|---|---|
| *G06T 7/90* | (2017.01) |
| *G06T 17/00* | (2006.01) |
| *G06T 7/50* | (2017.01) |
| *G06T 7/70* | (2017.01) |
| *G06K 9/62* | (2022.01) |
| *G06T 17/20* | (2006.01) |
| *G16H 10/60* | (2018.01) |
| *G16H 30/20* | (2018.01) |
| *A61B 5/00* | (2006.01) |
| *G06V 10/40* | (2022.01) |
| *G06V 10/42* | (2022.01) |
| *G06V 20/64* | (2022.01) |
| *G06V 40/10* | (2022.01) |
| *G06V 40/20* | (2022.01) |
| *G06V 20/62* | (2022.01) |

(52) U.S. Cl.
CPC ......... *G06K 9/6256* (2013.01); *G06K 9/6265* (2013.01); *G06T 7/0012* (2013.01); *G06T 7/50* (2017.01); *G06T 7/70* (2017.01); *G06T 7/90* (2017.01); *G06T 17/00* (2013.01); *G06T 17/20* (2013.01); *G06V 10/40* (2022.01); *G06V 10/42* (2022.01); *G06V 20/62* (2022.01); *G06V 20/64* (2022.01); *G06V 40/10* (2022.01); *G06V 40/20* (2022.01); *G16H 10/60* (2018.01); *G16H 30/20* (2018.01); *G06T 2200/08* (2013.01); *G06T 2207/10024* (2013.01); *G06T 2207/20081* (2013.01); *G06T 2207/20084* (2013.01); *G06T 2207/30004* (2013.01); *G06T 2207/30196* (2013.01); *G06V 2201/033* (2022.01)

(58) Field of Classification Search
CPC .... A61B 5/70; A61B 5/0077; G06K 9/00201; G06K 9/00335; G06K 9/00362; G06K 9/46; G06K 9/52; G06K 9/6217; G06K 9/6256; G06K 9/6265; G06K 2209/055; G06K 9/627; G06K 9/00369; G06K 9/00342; G06K 9/6268; G06K 2209/05; G06T 7/0012; G06T 7/50; G06T 7/70; G06T 7/90; G06T 17/00; G06T 17/20; G06T 2200/08; G06T 2207/10024; G06T 2207/20081; G06T 2207/20084; G06T 2207/30004; G06T 2207/30196; G06N 3/0454; G06N 3/084

See application file for complete search history.

(56) References Cited

U.S. PATENT DOCUMENTS

| | | | |
|---|---|---|---|
| 2011/0201916 A1* | 8/2011 | Duyn | A61B 5/721 600/410 |
| 2012/0310666 A1* | 12/2012 | Xu | G16H 10/60 705/3 |
| 2016/0157938 A1* | 6/2016 | Breisacher | G16H 30/20 382/128 |
| 2019/0096520 A1* | 3/2019 | Strobel | G06T 7/149 |
| 2019/0147340 A1* | 5/2019 | Zhang | G06N 3/0454 706/25 |
| 2019/0251723 A1* | 8/2019 | Coppersmith, III | G06T 11/60 |

OTHER PUBLICATIONS

Zhou et al., "Towards 3D Human Pose Estimation in theWild: aWeakly-supervised Approach", CVF, 2017, pp. 398-407.
Zimmermann et al., "3D Human Pose Estimation in RGBD Images for Robotic Task Learning",arXiv:1803.02622v2 [cs.CV] Mar. 13, 2018, pp. 1-7.
Guler et al., "DensePose: Dense Human Pose Estimation in the Wild", 2018, CVF, pp. 7297-7306.
Arnab et al., "Exploting Temporal Context for 3D Human Pose Estimation in the Wild", 2019, CVF, pp. 3395-3404.
Bahdanau et al., "Neural Machine Translation by Jointly Learning to Align and Translate", ICLR, 2015, arXiv:1409.0473v7 [cs.CL], pp. 1-15.
Belghit et al., "Vision-Based Pose Estimation for Augmented Reality: A Comparison Study", IEEE, 2018, pp. 1-8.
Bogo et al., "Keep It SMPL: Automatic Estimation of 3D Human Pose and Shape from a Single Image", Computer Vision and Pattern Recognition, 2016, pp. 561-578.
Cao et al., "Realtime Multi-Person 2D Pose Estimation Using Part Affinity Fields", CVF, 2017, pp. 7291-7299.
Chen et al., 3D Human Pose Estimation + 2D Pose Estimation + Matching, CVF, 2016, pp. 7035-7043.
Chen et al., "Synthesizing Training Images for Boosting Human 3D Pose Estimation", arXiv:1604.02703v6 [cs.CV] Jan. 5, 2017, pp. 4321-4330.
Chen et al., "Weakly-Supervised Discovery of Geometry-Aware Representation for 3D Human Pose Estimation", CVF, 2019, p. 10895-10904.
Liu et al., "PKU-MMD: A Large Scale Benchmark for Continuous Multi-Modal Human Action Understanding", arXiv:1703.07475V2 [cs.CV] Mar. 28, 2017, pp. 1-10.
Deprelle et al., "Learning Elementary Structures for 3D Shape Generation and Matching", arXiv:1908.04725v2 [cs.CV] Aug. 14, 2019, pp. 1-11.
Groueix et al., "3D-Coded: 3D Correspondences by Deep Deformation", CVF, 2018, pp. 1-17.
Gupta et al., "3D Pose from Motion for Cross-View Action Recognition via Non-linear Circulant Temporal Encoding", CVF, 2014, pp. 1-8.
He et al., "Deep Residual Learning for Image Recognition", CVF, 2015, pp. 770-778.
He et al., "Identity Mappings in Deep Residual Networks", arXiv:1603.05027v3 [cs.CV] Jul. 25, 2016. pp. 1-15.
Jahangiri et al., "Generating Multiple Diverse Hypotheses for Human 3D Pose Consistent with 2D Joint Detections", IEEE, 2017, pp. 805-814.
Hao Jiang, "3D Human Pose Reconstruction Using Millions of Exemplars", International Conference on Pattern Recognition, 2010, pp. 1674-1677.
Johnson et al., "Clustered Pose and Nonlinear Appearance Models for Human Pose Estimation", BMVC, 2010, pp. 1-11.
Kadkhodamohammadi et al., "A Multi-View RGB-D Approach for Human Pose Estimation in Operating Rooms," IEEE, 2017, pp. 363-372.
Kanazawa et al., "End-To-End Recovery of Human Shape and Pose", CVF, 2017, pp. 7122-7131.
Kanazawa et al., "Learning 3D Human Dynamics from Video", CVF, 2019, pp. 5614-5623.
Kocabas et al., "Self-Supervised Learning of 3D Human Pose Using Multi-View Geometry", CVF, 2019, pp. 1077-1086.
Kohli et al., "Key Developments in Human Pose Estimation for Kinect", Advances in Computer Vision and Pattern Recognition, 2013, pp. 63-70.
Kolotouros et al., "Convolutional Mesh Regression for Single-Image Human Shape Reconstruction", CVF, 2019, pp. 4501-4510.
Lassner et al., "Unite the People: Closing the Loop Between 3D and 2D Human Representations", CVF, 2017, pp. 6050-6059.
Levine et al., "End-To-End Training of Deep Visuomotor Policies", Journal of Machine Learning Research 17, 2016, pp. 1-40.
Liang et al., "Shape-Aware Human Pose and Shape Reconstruction Using Multi-View Images", CVF, 2019, pp. 4352-4362.
Lin et al., "Microsoft COCO: Common Objects in Context", Springer International Publishing Switzerland, 2014, pp. 740-755.
Looper et al., "MoSh: Motion and Shape Capture from Sparse Markers", ACM Transactions on Graphics, vol. 33, No. 6, 2014, pp. 1-13.
Looper et al., "SMPL: A Skinned Multi-Person Linear Model", ACM Transactions on Graphics, 2015, pp. 1-16.

(56) References Cited

OTHER PUBLICATIONS

Martinez et al., "A Simple Yet Effective Baseline for 3D Human Pose Estimation", CVF, 2017, pp. 2640-2649.
Martinez-Gonzalez et al., "Reall-time Convolutional Networks for Depth-Based Human Pose Estimation", IDIAP Research Institute, 2018, pp. 1-7.
Mehta et al., "VNect: Real-time 3D Human Pose Estimation with a Single RGB Camera", ACM Transactions on Graphics, vol. 36, No. 4, 2017, pp. 1-14.
Moeslund et al., "A Survey of Computer Vision-Based Human Motion Capture" Computer Vision and Image Understanding 81, 2001, pp. 231-268.
Moeslund et al., "A Survey of Advances in Vision-Based Human Motion Capture", Elsevier, 2006, pp. 90-126.
Newell et al., "Stacked Hourglass Networks for Human Pose Estimation", arXiv:1603.06937v2 [cs.CV] Jul. 26, 2016, pp. 1-17.
Obdrzalek et al., "Accuracy and Robustness of Kinect Pose Estimation in the Context of Coaching of Elderly Population", IEEE, 2012, pp. 1188-1193.
Paszke et al., "Automatic Differentiation in PyTorch" 31st Conference on Neural Information Processing Systems, 2017, pp. 1-4.
Pavlakos et al., "Ordinal Depth Supervision for 3D Human Pose Estimation", CVF, 2018, pp. 7307-7316.
Pavlakos et al., "Coarse-To-Fine Volumetric Prediction for Single-Image 3D Human Pose", CVF, 2017, pp. 7025-7034.
Peng et al., "Jointly Optimize Data Augmentation and Network Training Adversarial Data Augmentation in Human Pose Estimation", CVF, 2018, pp. 2226-2234.
Rhodin et al., "Neural Scene Decomposition for Multi-Person Motion Capture", CVF, 2019, pp. 7703-7713.
Rhodin et al., "Unsupervised Geometry-Aware Representation for 3D Human Pose Estimation", CVF 2018, pp. 1-18.
Rogez et al., "MoCap-Guided Data Augmentation for 3D Pose Estimation in the Wild", Computer Vision and Pattern Recognition, 2016, pp. 1-9.
Sarafianos et al., "3D Human Pose Estimation: A Review of the Literature and Analysis of Covariates" Elsevier, Computer Vision and Image Understanding, 2016, pp. 1-20.
Sharma et al., "Monocular 3D Human Pose Estimation by Generation and Ordinal Ranking", CVF, 2019, pp. 2325-2334.
SUN et al., "Integral Human Pose Regression" CVF, 2018, pp. 1-17.
Sung et al., "Unstructured Human Activity Detection from RGBD Images", IEEE, 2012, pp. 1-8.
Varol et al., "Learning from Synthetic Humans", CVF, 2017, pp. 109-117.
Wandt et al., "RepNet: Weakly Supervised Training of an Adversarial Reprojection Network for 3D Human Pose Estimation", CVF, 2019, pp. 7782-7791.

\* cited by examiner

PERSONALIZED PATIENT POSITIONING, VERIFICATION AND TREATMENT

CROSS-REFERENCE TO RELATED APPLICATIONS

This application claims the benefit of Provisional U.S. Patent Application No. 62/941,203, filed Nov. 27, 2019, the disclosure of which is incorporated herein by reference in its entirety.

BACKGROUND

Medical diagnosis and treatment are personal in nature and generally require customized instructions or guidance for each patient. For example, in radiation therapy and medical imaging (e.g., X-ray photography, magnetic resonance imaging (MRI), computer tomography (CT), and positron emission tomography (PET)), success largely depends on the ability to maintain the patient in a desirable position according to the patient's physical characteristics so that scanning or treatment delivery may be performed in a precise and accurate manner. Conventional positioning techniques generally require manual adjustments of the patient's position, placement of markers on or near the patient's body, or the conduction of simulation sessions in order to determine the optimal operating parameters and/or conditions for the patient. These techniques are not only cumbersome but also lack accuracy, consistency, and real-time monitoring capabilities.

At the same time, medical facilities such as hospitals are often in possession of an abundant collection of medical records that relate to a patient's diagnostic records, treatment plans, scan images, etc. These medical records can offer valuable insights into the patient's medical history as well as ways to enhance the patient's healthcare experiences. Therefore, it is highly desirable that these medical records be utilized to personalize the way healthcare services are provided. Further, given the unique circumstances associated with medical facilities, it is also very important that these personalized services be provided in an accurate, secure, and automated fashion to minimize the risks of human errors, cross-contamination, breach of privacy, etc.

SUMMARY

Described herein are systems, methods and instrumentalities for providing personalized healthcare services to a patient. In examples, such a system may include one or more repositories configured to store electronic medical records of the patient. The electronic medical records may comprise imagery data and/or non-imagery data associated with a medical procedure performed or to be performed for the patient. The imagery and/or non-imagery data may be retrieved by a processing unit of the system and used to generate personalized medical assistance information relating to the patient. For instance, the processing unit may be configured to receive one or more images of the patient and extract a plurality of features from the images that collectively represent a characteristic of the patient. Based on at least one of these extracted features, the processing unit may determine the identity of the patient and retrieve the imagery and/or non-imagery data from the one or more repositories. The personalized medical assistance information thus created may include a parameter (e.g., a medical imaging parameter or an operating parameter of a medical device) associated with the medical procedure, positioning information pertaining to the medical procedure, and/or overlaid scan images and pictures of the patient showing a diagnostic or treatment history of the patient. The personalized medical assistance information may be presented to the patient or a service provider via a display device to assist the patient or the service provider during a healthcare service.

The images described herein may be a photo of the patient taken by a camera, a thermal image of the patient generated by a thermal sensor, and/or the like. The features extracted from these images may be matched against a set of known features of the patient stored in a feature database. The features may also be processed through a neural network trained for visual recognition. Further, the imagery data stored in the repositories may include a depiction of an incorrect position for the medical procedure and the personalized medical assistance information may include instructions for how to avoid the incorrection position. The overlaid scan images and pictures of the patient may be generated by determining a respective scan position associated with each image and aligning the image with a picture of the patient in a substantially similar position. The resulting representation may be suitable for display in an augmented reality (AR) environment to enhance the experience of the patient or service provider.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
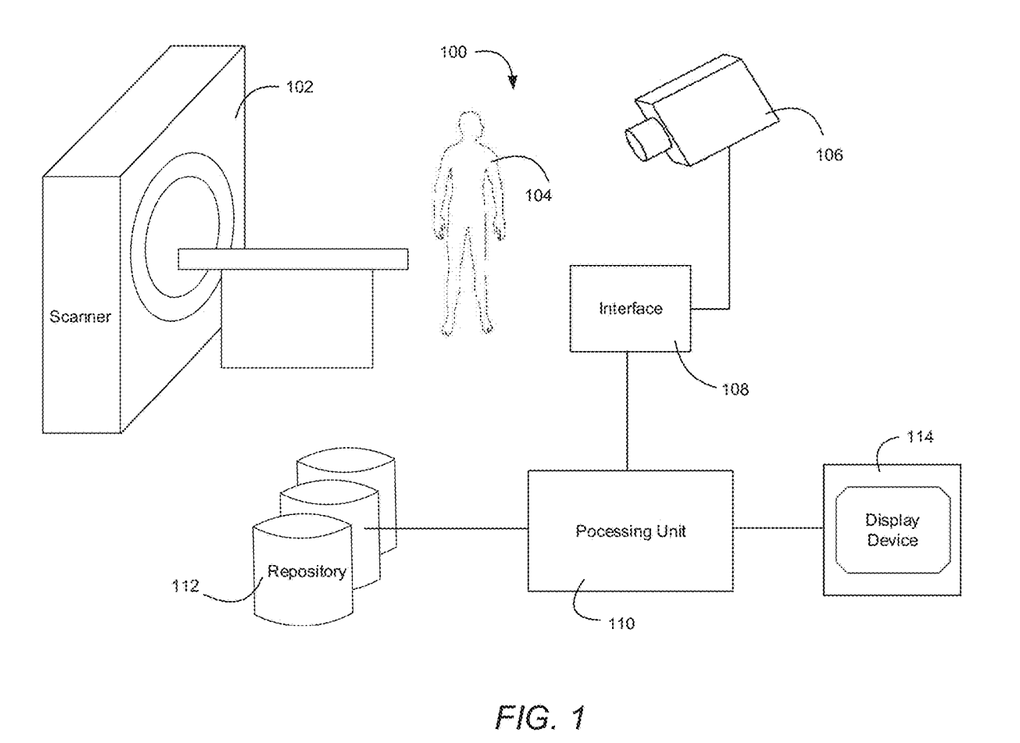
FIG. 1 is a simplified diagram illustrating an example system for providing personalized healthcare services as described herein.

FIG. 1 is a diagram of an example system 100 for providing personalized healthcare services at a medical facility such as a hospital. These healthcare services may include, for example, an imaging procedure conducted via a scanner 102 (e.g., a CT scanner, an MRI machine, a PET scanner, etc.) or radiation therapy delivered through a medical linear accelerator (LINAC) (not shown). Such services may require precise knowledge of the patient's anatomical characteristics and/or that the patient stay in a particular position or pose to enhance the precision and/or efficiency of the scan or treatment. For example, proper positioning of the patient may ensure that a target scan area of the patient is adequately and clearly captured, and/or that the patient is not exposed to unnecessary radiation during the treatment. At the same time, a medical professional planning or performing the medical procedure may also desire to access the patient's personal medical information in order to obtain an accurate assessment of the patient's conditions or design an appropriate plan or protocol for the procedure.

The system 100 may facilitate the provision of the personalized services described above by automatically recognizing the recipient of the services (e.g., a patient 104) and constructing a medical profile for the patient based on the patient's historical medical records. For example, the system 100 may include a sensing device 106 (e.g., an image capturing device) configured to capture images of the patient in or around a medical facility. The sensing device 106 may comprise one or more sensors such as a camera, a red, green and blue (RGB) sensor, a depth sensor, a thermal sensor, and/or an infrared (FIR) or near-infrared (NIR) sensor configured to detect the patient's presence and generate an image of the patient in response. Depending on the type of sensing device used, the image may be, for example, a photo of the patient taken by a camera or a thermal image of the patient generated by a thermal sensor. The sensing device 106 may be installed in various locations of the medical facility such as inside a treatment room, over a doorway, on an imaging device, etc. Alternatively or additionally, the sensing device 106 may comprise a scanner configured to obtain the image of the patient based on an existing photo of the patient (e.g., a driver's license presented by the patient during check-in).

The image of the patient produced by the sensing device 106 may represent one or more characteristics of the patient. Such characteristics may include, for example, facial features of the patient, a body contour of the patient, a walking pattern of the patient, etc. These characteristics of the patent may be recognized by a processing device based on features extracted from the image, as explained in more detail below.

The system 100 may include an interface unit 108 configured to receive the image of the patient produced by the sensing device 106. The interface unit 108 may be communicatively coupled to the sensing device 106, for example, over a wired or wireless communication link. The interface unit 108 may be configured to retrieve or receive images from the sensing device 106 on a periodic basis (e.g., once every of minute, according to a schedule, etc.), or the interface unit 108 may be configured to receive a notification from the sensing device 106 when an image has been generated and retrieve the image from the sensing device in response to receiving the notification. The sensing device 106 may also be configured to transmit images to the interface unit 108 without first sending a notification.

The interface unit 108 may operate as a pre-processor for the images received from the sensing device 108. For example, the interface unit 108 may be configured to reject images that are of poor quality or convert the received images into a suitable format so that they may be further processed by a downstream component of the system 100. The interface unit 108 may also be configured to prepare the images in ways that would reduce the complexity of downstream processing. Such preparation may include, for example, converting color images to grayscale, resize the images into unified dimensions, and/or the like. Further, although the interface unit 108 is shown in FIG. 1 as being separate from the other components of the system 100, the interface unit 108 may also be a part of the other components. For example, the interface unit 108 may be comprised in the sensing device 106 or in a processing unit 110 without affecting the functionality of the interface unit 108 described herein.

The images of a patient produced by the sensing device 106 and/or the interface unit 108 may be used to build a medical profile for the patient, for example, automatically upon detecting the patient at a medical facility or inside a treatment room. As such, manual operations involved in the process may be minimized or reduced, eliminating the risks of human errors, unnecessary exposure to contamination or radiation, etc. The speed of service may also improve as a result.

The system 100 may include a processing unit 110 capable of providing the aforementioned improvements. The processing unit 110 may be communicatively coupled to the sensing device 106 and/or the interface unit 108 to receive the images of the patient. The processing unit 110 may be configured to extract features from the images that collectively represent a characteristic of the patient and compare the extracted features against a set of known features of the patient to determine the identity of the patient. Alternatively or additionally, the processing unit 110 may utilize an artificial neural network trained to take the images of the patient as inputs and produce an output indicating the patient's identity. Such a neural network may be a convolutional neural network (CNN) comprising a cascade of layers each trained to make pattern matching decisions based on a respective level of abstraction of visual characteristics contained in an image. Training may be performed to the CNN using various datasets and loss functions so that the CNN becomes capable of extracting features (e.g., in the form of feature vectors) from an input image, determining whether the features match those of a known person, and indicating the matching results at the output of the network. Example implementations of the neural network and patient recognition will be described in greater detail below.

The system 100 may further include at least one repository 112 (e.g., one or more repositories or databases) configured to store patient medical information (e.g., medical records). These medical records may include general patient information (e.g., patient ID, name, electronic and physical address, insurance, etc.), non-imagery medical data (e.g., diagnostic history of the patient, treatments received by the patient, scan protocols, medical metadata, etc.) associated with a medical procedure performed or to be performed for the patient, and/or imagery data associated with the medical procedure. In examples, the imagery data may include scan images of the patient (e.g., MRI, CT scan, X-ray, Ultrasound, etc.), visual representations of the positions (e.g., correct or incorrect positions) taken by the patient during those scans, visual representations of the adjustments made by the patient to get into a correction position, etc.

The medical records may be stored in the repository 112 in a structured fashion (e.g., arranged in a certain format or pattern). The records may be collected from a plurality of sources including, for example, hospitals, doctors' offices, insurance companies, etc. The records may be collected and/or organized by the system 100, by another system at the medical facility, or by a different organization (e.g., the medical records may exist independent of the system 100). The collection and/or organization of the medical records may be performed in an offline manner or may be carried out when the repository 112 is actively being accessed (e.g., online) by other systems or applications.

The repository 112 may be hosted on one or more database servers that are coupled to the processing unit 110 via a wired or wireless communication link (e.g., a private computer network, a public computer network, a cellular network, a service cloud, etc.). The wired or wireless communication link may be secured via encryption, virtual private network (VPN), Secure Socket Layer (SSL), and/or the like to ensure the safety of the medical information stored therein. The repository 112 may also utilize a distributed architecture such as one built with blockchain technologies.

The medical records stored in the repository 112 may be used to personalize the healthcare services provided to a patient. For instance, in response to recognizing a patient based on one or more images of the patient, the processing unit 110 may retrieve all or a subset of the patient's medical records including the imagery and/or non-imagery data described above from the repository 112 and use the information to generate personalize medical assistance information (e.g., a medical profile) for the patient. The personalize medical assistance information may indicate, for example, a procedure that the patient is about to undertake and historical data associated with the procedure, such as scan images of the patient from a similar procedure performed in the past, position(s) taken by the patient during that procedure, adjustments or corrections made to get the patient into a desired or correct position, etc. The personalize medical assistance information may also include one or more parameters associated with the procedure such as imaging parameters (e.g., image dimensions, voxel size, repetition time, etc.) and/or operating parameters of a medical device used in the procedure (e.g., height, orientation, power, dosage, etc.). Such information may provide guidance and insight for the patient with respect to what may be required (e.g., in terms of positioning) for the upcoming procedure.

The medical profile described herein may also be used to assist a medical professional in providing personalized services to the patient. For instance, the personalized medical assistance information described herein may include a diagnostic or treatment history of the patient that the medical professional may use to assess the patient's conditions. The diagnostic or treatment history may comprise previous scan images of the patient taken at different times. Each of the scan images may be characterized by at least one positioning parameter indicating the position of the patient during the scan. The positioning parameter may be extracted, for example, from the metadata associated with each scan image. When generating the personalized medical assistance information described herein, the processing unit 110 may align these scan images of the patient with pictures or models (e.g., a 3D mesh model) of the patient depicting the patient in substantially similar positions as those taken by the patient when the scan images were created. In examples, the pictures may be captured by an image capturing device such as the sensing device 106, and the models may be constructed based on the pictures (e.g., utilizing neural networks and/or parametric model building techniques for deriving human models from 2D images). The processing unit 110 may then generate a visual representation for each pair of aligned picture (or model) and scan image in which the picture (or model) of the patient is overlaid with the scan image of the patient. The visual representations thus generated may demonstrate changes (or lack thereof) in a diseased area of the patient over time and do so with a higher level of accuracy, since each scan image is shown against a background containing a depiction of the patient in a similar position as the scan position.

Parts or the entirety of the personalized medical assistance information (e.g., the medical profile) described above may be visually presented to the patient or a medical professional through a display device 114. The display device 114 may include one or more monitors (e.g., computer monitors, TV monitors, tablets, mobile devices such as smart phones, etc.), one or more speakers, one or more augmented reality (AR) devices (e.g., AR goggles), and/or other accessories configured to facilitate visual representation. The display device 114 may be communicatively coupled to the processing unit 110 (e.g., via a wired or wireless communication link) and configured to display the personalized medical assistance information generated by the processing unit 110. As described herein, such personalized medical assistance information may include basic patient information, desired configurations for an upcoming medical procedure (e.g., according to a corresponding scan protocol designed for the patient), scan images previously taken for the patient, positions of the patient during those scans, adjustments or corrections made to get the patient into a desired scan position, overlaid scan images and pictures (or models) of the patient, etc. The personalized medical assistance information may be displayed in various formats including, for example, videos, animations, and/or AR presentations. For example, the overlaid representations of the patient's scan images and pictures may be displayed in an AR environment in which a physician equipped with AR glasses and/or an AR input device may swipe through the representations in a stereoscopic manner.

Figure 2:
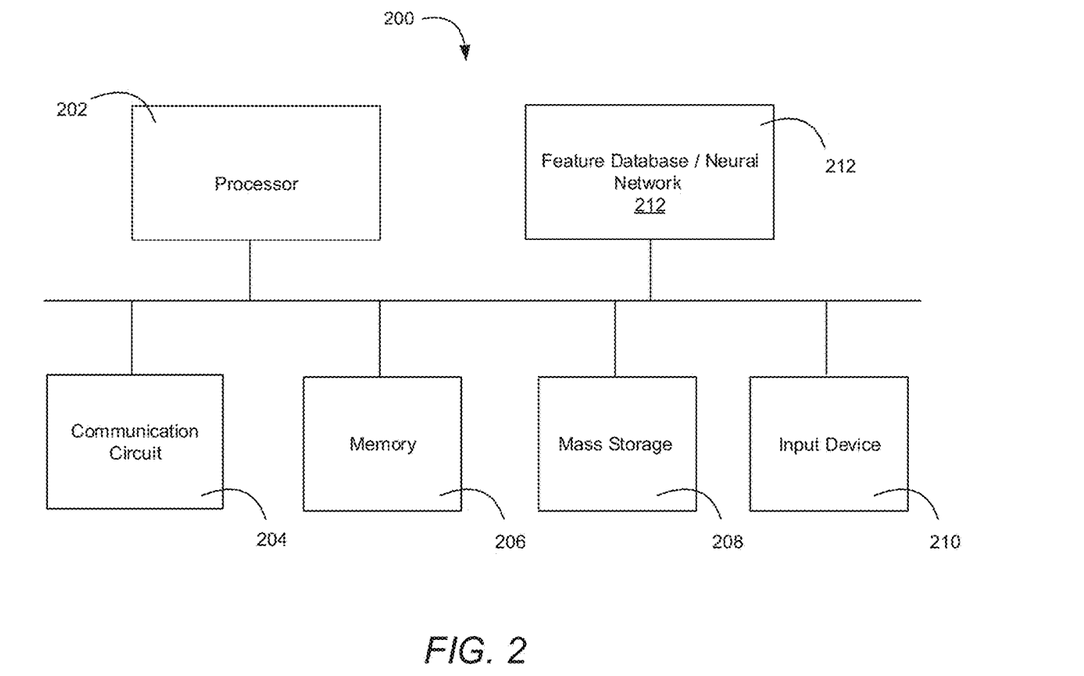
FIG. 2 is a simplified block diagram illustrating an example processing unit as described herein.

FIG. 2 is a simplified block diagram illustrating an example processing unit 200 (e.g., the processing unit 110) as described herein. The processing unit 200 may operate as a standalone device or may be connected (e.g., networked or clustered) with other computation devices to perform the functions described herein. In an example networked deployment, the processing unit 200 may operate in the capacity of either a server or a client device in server-client network environments, or it may act as a peer device in peer-to-peer (or distributed) network environments. Further, while only a single unit is shown in FIG. 2, the term "processing unit" shall be taken to potentially include multiple units or machines that individually or jointly execute a set of instructions to perform any one or more of the functions discussed herein. The multiple units or machines may belong to one location or multiple locations, for example, under a distributed computing architecture.

The processing unit 200 may include at least one processor (e.g., one or more processors) 202 which in turn may include a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. The processing unit 200 may further include a communication circuit 204, a memory 206, a mass storage device 208 and/or an input device 210. The communication circuit 204 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). The memory 206 may include a machine-readable medium configured to store instructions that, when executed, cause the processor 202 to perform one or more of the functions described herein. Examples of a machine-readable medium may include volatile or non-volatile memory including but not limited to semiconductor memory (e.g., electrically programmable read-only memory (EPROM), electrically erasable programmable read-only memory (EEPROM)), flash memory, and/or the like. The mass storage device 208 may include one or more magnetic disks such as internal hard disks, removable disks, magneto-optical disks, CD-ROM or DVD-ROM disks, etc., on which instructions and/or data may be stored to facilitate the performance of the functions described herein. The input device 210 may include a keyboard, a mouse, a voice-controlled input device, a touch sensitive input device (e.g., a touch screen), and/or the like for receiving user inputs to the processing unit 200.

In an example implementation, the processing unit 200 may include or may be coupled to a feature database 212 configured to store images of a patient and/or visual representations of one or more characteristics of the patients (e.g., known features of the patient). The images and/or visual representations may be prepared (e.g., pre-computed) and stored in the feature database 212 based on imagery data of the patients collected from various sources including, for example, pictures taken during the patients' past visits to a medical facility, repositories storing the patient's medical records (e.g., the repository 112 shown in FIG. 1), a public photo ID database (e.g., a driver license database), etc. The database 212 may be communicatively coupled to the processor 202 and used by the processor to identify a patient based on images of the patient obtained through a sensing device (e.g., the sensing device 106 of FIG. 1). For example, the processor 202 may be configured to receive an image of the patient from the sensing device and extract a set of features from the image that collectively represent a characteristic of the patient. The processor 202 may be further configured to match at least one of the extracted features against the imagery data (e.g., known features of the patient) stored in the feature database 212 to determine an identity of the patient.

The features and/or characteristics described herein may be associated with a variety of attributes of the patient such as body contour, height, facial features, walking patterns, poses, etc. In the context of digital imagery, these features or characteristics may correspond to structures in an image such as points, edges, objects, etc. Various techniques may be employed to extract these features from the image. For example, one or more keypoints associated with a feature may be identified including points at which the direction of the boundary of an object changes abruptly, intersection points between two or more edge segments, etc. These keypoints may be characterized by well-defined positions in the image space and/or stability to illumination/brightness perturbations. As such, the keypoints may be identified based on image derivatives, edge detection, curvature analysis, and/or the like.

Once identified, the keypoints and/or the feature associated with the keypoints may be described with a feature descriptor or feature vector. In an example implementation of such feature descriptor or vector, information related to the feature (e.g., appearance of the local neighborhood of each keypoint) may be represented by (e.g., encoded into) a series of numerical values stored in the feature descriptor or vector. The descriptor or vector may then be used as a "fingerprint" for differentiating one feature from another or matching one feature with another.

Reverting back to the example shown in FIG. 2, the processor 202 may be configured to determine what specific features are to be extracted from a received image of the patient, extract those features from the image (e.g., generate one or more feature vectors corresponding to the features), and determine the identity of the patient by matching at least one of the extracted features against the imagery data stored in the feature database 212. The processor may determine which one or more of the extracted features are to be used to determine the patient's identity base on, for example, a user input or a configuration (e.g., a system configuration parameter). Further, the processor 202 may be configured to determine that certain areas of the patient's body are obstructed or occluded, and subsequently avoid using features associated with the obstructed areas for patient matching (e.g., the processor 202 may decide to use a different feature such as the walking pattern of the patient for identifying the patient). Obstructed or occluded areas of the patient may be determined, for example, by running occlusion detectors for one or more parts of the patient body (e.g., in a bottom-up manner), and/or by recognizing the overall pose of the patient and then inferring the occluded areas based on the overall pose of the patient. Depth information associated with one or more images of the patient may be used to determine the obstructed or occluded areas. The processor 202 may be also configured to use features associated with an obstructed area for patient matching and provide an indication that such matching may not be robust (e.g., give the matching a low confidence score).

In an example implementation, the processing unit 200 may comprise a neural network in addition to or instead of the feature database 212 for identifying a patient based on images obtained through a sensing device (e.g., the sensing device 106). The neural network may be a convolutional neural network (CNN) or a deep neural network (DNN) that comprises multiple layers (e.g., an input layer, one or more convolutional layers, one or more pooling layers, one or more fully connected layers, and/or an output layer). Each of the layers may correspond to a plurality of filters (or kernels), and each filter may be designed to detect a specific type of visual features. The filters may be associated with respective weights that, when applied to an input, produce an output indicating whether certain visual features have been detected. The weights associated with the filters may be learned by the neural network through a training process that comprises inputting images of patients from a training dataset to the neural network (e.g., in a forward pass), calculating losses resulting from the weights currently assigned to the filters based on a loss function (e.g., a margin based loss function), and updating (e.g., in a backward pass) the weights assigned to the filters to minimize the losses (e.g., based on stochastic gradient descent). Once trained, the neural network may be able to take an image of the patient at the input layer, extract and/or classify visual features of the patient from the image, and provide an indication at the output layer regarding whether the input image matches that of a known patient.

In either of the examples described above, once a matching patient is found, the processor 202 may proceed to query a repository (e.g., the repository 112 in FIG. 1) to retrieve medical records (e.g., imagery and/or non-imagery data associated with a medical procedure) of the patient based on the patient's identity. The medical records may include, for example, positioning information associated with a medical procedure to be performed for the patient, previous scan pictures or other types of images of the patient, diagnostic and treatment history of the patient, etc. The processor 202 may generate personalized medical assistance information (e.g., build a medical profile) for the patient based on the retrieved medical records. The processor 202 may further display parts or the entirety of the personalized medical assistance information to the patient or a medical professional via a graphical user interface, e.g., as described in association with FIG. 1.

Figure 3A:
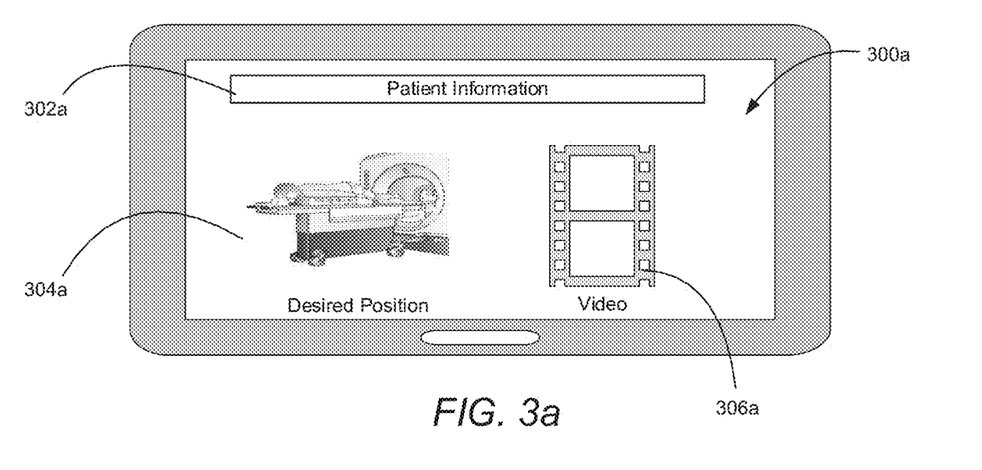
FIGS. 3a and 3b are illustrations of examples graphical user interfaces (GUIs) for presenting personalized medical assistance information to a patient or a service provider.
Figure 3B:
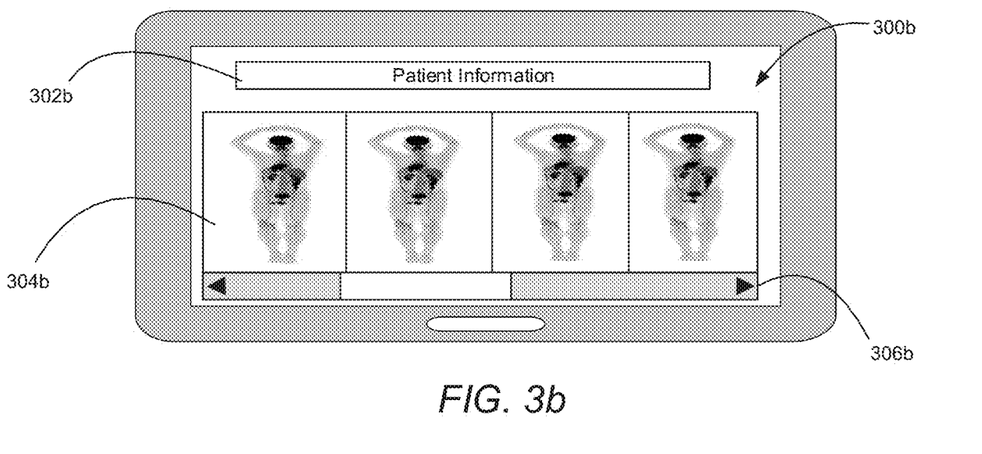

FIGS. 3a and 3b are diagrams illustrating example graphical user interfaces (GUIs) for presenting personalized medical assistance information to a patient or a medical professional in response to identifying the patient based on one or more images. FIG. 3a shows a first example GUI 300a for presenting the personalized medical assistance information.

The GUI 300a may include areas 302a, 304a and/or 306a. The area 302a may be configured to display basic patient information such as patient name, date of birth, time of the patient's last hospital visit, diagnoses, prescriptions, etc. The area 304a may be configured to display a desired position of the patient for an upcoming medical procedure (e.g., an MRI scan), and the area 306a may be configured to show positions (e.g., correct and/or incorrect positions) previously taken by the patient during similar procedures and/or adjustments made by the patient to get into a desired position. The position and/or adjustment information may be presented in various formats including, for example, videos or animations.

FIG. 3b shows a second example GUI 300b for presenting the personalized medical assistance information described herein. The GUI 300b may include areas 302b, 304b and/or 306b. The area 302b in FIG. 3b may be configured to display basic patient information, similar to the area 302a in FIG. 3a, and the area 304b may be configured to display a diagnostic or treatment history of the patient such as scan images of the patient overlaid with pictures or models of the patient in corresponding scan positions, as described herein. A service provider (e.g., a doctor) may browse through the presented information, for example, using a scroll bar 306b.

Figure 4:
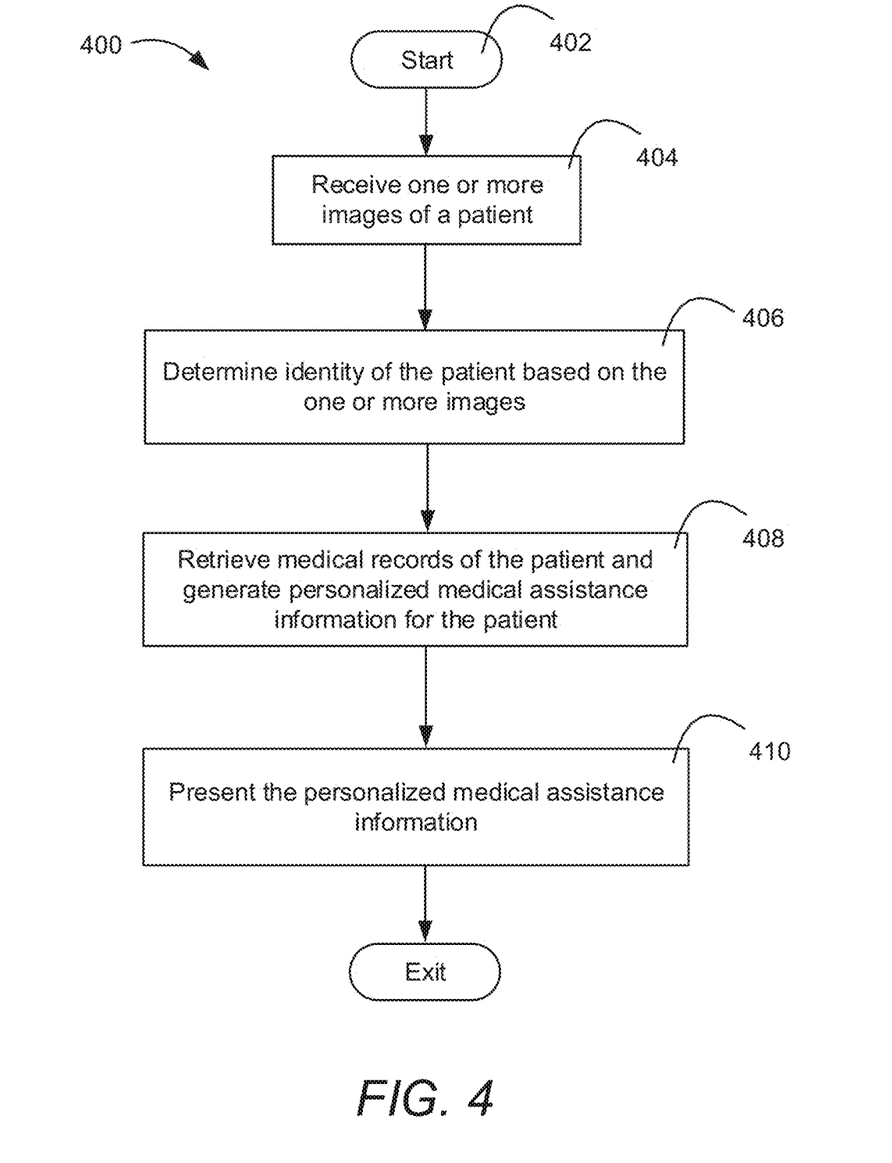
FIG. 4 is a flow diagram illustrating a method that may be implemented by the personalized healthcare system depicted in FIG. 1.

FIG. 4 is a flow diagram illustrating a method 400 that may be implemented by a personalized healthcare system described herein (e.g., the system 100 of FIG. 1). For simplicity of explanation, the operations in the method 400 are depicted and described herein with a specific order. It should be appreciated, however, that these operations may occur in various orders and/or concurrently, and with other operations not presented and described herein. Furthermore, not all illustrated operations may be required to implement the method disclosed herein.

The method 400 may be started by a processing unit of the personalized healthcare system (e.g., the processing unit 110 of FIG. 1 or 200 of FIG. 2) at 402. At 404, the processing unit may receive one or more images of a patient from a sensing device (e.g., the sensing device 106 of FIG. 1). Such images may include a camera photo, a thermal image, and/or the other types of imagery that depict the characteristics of the patient. At 406, the processing unit may analyze the received image(s) and determine the identity of the patient based on at least one of the features extracted from the image(s). The analysis and/or identification may be performed, for example, by matching the at least one of the extracted features against known features of the patient stored in a feature database and/or utilizing a neural network trained for visual recognition, as described herein. Once the identity of the patient has been determined, the processing unit may, at 408, retrieve medical records (e.g., imagery and/or non-imagery data) of the patient from one or more repositories (e.g., the repository 112 in FIG. 1) and use those records to generate personalized medical assistance information (e.g., such as a medical profile) for the patient. The personalized medical assistance information may then be used at 410 to provide personalized healthcare services to the patient including, for example, positioning assistance, scan image review, medical history analysis, etc.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "segmenting", "analyzing", "determining", "enabling", "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A system for providing personalized healthcare services, comprising:
   one or more repositories configured to store electronic medical records of a patient, the electronic medical records comprising imagery data associated with a medical procedure performed or to be performed for the patient, the imagery data including a depiction of an incorrect position associated with the medical procedure; and
   a processing unit configured to:
      receive one or more images of the patient;
      extract, from the one or more images of the patient, a plurality of features that collectively represent a characteristic of the patient;
      determine an identity of the patient based on at least one of the extracted features;
      retrieve the imagery data from the one or more repositories in response to determining the identity of the patient; and
      generate personalized medical assistance information relating to the patient based on the imagery data retrieved from the one or more repositories, wherein the personalized medical assistance information comprises instructions for how to avoid the incorrect position associated with the medical procedure.

2. The system of claim 1, wherein the one or more images of the patient comprise a photo of the patient taken by a camera or a thermal image of the patient generated by a thermal sensor.

3. The system of claim 1, further comprising a display device configured to present the personalized medical assistance information, wherein the presentation comprises a visual depiction of a current position of the patient for the medical procedure.

4. The system of claim 1, wherein the characteristic of the patient comprises a walking pattern of the patient.

5. The system of claim 1, wherein the processing unit being configured to determine the identity of the patient based on at least one of the extracted features comprises the processing unit being configured to match the at least one of the extracted features against known features of the patient stored in a feature database.

6. The system of claim 1, wherein the processing unit is configured to determine the identity of the patient based on at least one of the extracted features using a neural network trained for visual recognition.

7. The system of claim 1, wherein the personalized medical assistance information further comprises instructions for how to get into a desired position for the medical procedure.

8. The system of claim 1, wherein the imagery data includes one or more scan images of the patient relating to the medical procedure, each of the one or more scan images being associated with a scan position of the patient, and the processing unit being further configured to:
  align each of the one or more scan images of the patient with a picture of the patient depicting the patient in a position substantially similar to the scan position associated with the scan image;
  generate a visual representation for each pair of aligned scan image and picture of the patient by at least overlaying the picture of the patient with the scan image; and
  include the visual representation in the personalized medical assistance information.

9. The system of claim 8, further comprising an augmented reality (AR) display device, wherein the visual representation for each pair of aligned scan image and picture of the patient is suitable for display through the AR display device.

10. The system of claim 1, wherein the processing unit is further configured to determine which one or more of the extracted features are to be used to determine the identity of the patient based on a user input or a configuration.

11. The system of claim 1, wherein the personalized medical assistance information further includes a medical imaging parameter or an operating parameter of a medical device associated with the medical procedure.

12. A method for providing personalized healthcare services, the method comprising:
  receiving one or more images of a patient;
  extracting, from the one or more images of the patient, a plurality of features that collectively represent a characteristic of the patient;
  determining an identity of the patient based on at least one of the extracted features;
  retrieving imagery data from one or more repositories in response to determining the identity of the patient, wherein the imagery data is associated with a medical procedure and includes a scan image of the patient relating to the medical procedure, the scan image being associated with a scan position of the patient;
  aligning the scan image of the patient with a picture of the patient depicting the patient in a position that is substantially similar to the scan position associated with the scan image;
  creating a visual representation of the patient by overlaying the picture of the patient with the scan image;
  generating personalized medical assistance information relating to the patient based on the imagery data retrieved from the one or more repositories, wherein the personalized medical assistance information includes the visual representation of the patient created by overlaying the picture of the patient with the scan image; and
  presenting the personalized medical assistance information on a display device.

13. The method of claim 12, wherein the one or more images of the patient comprise a photo of the patient taken by a camera or a thermal image of the patient generated by a thermal sensor.

14. The method of claim 12, wherein determining the identity of the patient based on the at least one of the extracted features comprises matching the at least one of the extracted features with known features of the patient stored in a feature database.

15. The method of claim 12, wherein the identity of the patient is determined based on the at least one of the extracted features using a neural network trained for visual recognition.

16. The method of claim 12, wherein the personalized medical assistance information further comprises instructions for how to get into a desired position for the medical procedure and wherein presenting the personalized medical assistance information on the display device comprises presenting a visual depiction of the instructions on the display device.

17. The method of claim 12, further comprising presenting the visual representation of the patient in an augmented reality (AR) environment.

18. A device for providing personalized healthcare services, comprising:
  a processing unit configured to:
  receive one or more images of a patient;
  extract, from the one or more images of the patient, a plurality of features that collectively represent a characteristic of the patient;
  determine an identity of the patient based on at least one of the extracted features;
  retrieve imagery data from one or more repositories in response to determining the identity of the patient, wherein the imagery data is associated with a medical procedure performed or to be performed for the patient, and wherein the imagery data includes a depiction of an incorrect position associated with the medical procedure;
  generate personalized medical assistance information relating to the patient based on the imagery data retrieved from the one or more repositories, wherein the personalized medical assistance information comprises instructions for how to avoid the incorrect position associated with the medical procedure; and
  present the personalized medical assistance information.

* * * * *